(12) United States Patent
Giovanetti et al.

(10) Patent No.: US 7,417,166 B2
(45) Date of Patent: Aug. 26, 2008

(54) PROCESS FOR THE PREPARATION OF GABAPENTIN

(75) Inventors: Roberto Giovanetti, Schio (IT); Andrea Nicoli, Vicenza (IT); Massimo Verzini, Caldiero (IT); Giorgio Soriato, Caldiero (IT); Livius Cotarca, Cervignano del Friuli (IT)

(73) Assignee: Zach System S.p.A., Bresso (IT)

( * ) Notice: Subject to any disclaimer, the term of this patent is extended or adjusted under 35 U.S.C. 154(b) by 0 days.

(21) Appl. No.: 10/593,813

(22) PCT Filed: Mar. 21, 2005

(86) PCT No.: PCT/EP2005/051297

§ 371 (c)(1),
(2), (4) Date: Jul. 23, 2007

(87) PCT Pub. No.: WO2005/092837

PCT Pub. Date: Oct. 6, 2005

(65) Prior Publication Data

US 2007/0293700 A1 Dec. 20, 2007

(30) Foreign Application Priority Data

Mar. 25, 2004 (IT) .......................... MI2004A0579

(51) Int. Cl.
*C07C 61/08* (2006.01)

(52) U.S. Cl. .................................................... 562/507

(58) Field of Classification Search .............. None
See application file for complete search history.

(56) References Cited

U.S. PATENT DOCUMENTS

| 4,024,175 A | 5/1977 | Satzinger et al. |
| 5,068,413 A | 11/1991 | Steiner et al. |
| 5,091,567 A | 2/1992 | Geibel et al. |
| 6,846,950 B2 * | 1/2005 | Ferrari et al. ............... 562/507 |

FOREIGN PATENT DOCUMENTS

| WO | WO 98/28255 | 7/1998 |
| WO | WO 00/58268 | 10/2000 |
| WO | 02/34709 | 5/2002 |
| WO | WO 03/070683 | 8/2003 |
| WO | 03/089403 | 10/2003 |
| WO | 2004/110981 | 12/2004 |

OTHER PUBLICATIONS

Solomons, Organic Chemistry, 5th edition, 1992, John Wiley & Sons, Inc., New York, pp. 762-764.*
U.S. Appl. No. 10/593,813, filed Sep. 22, 2006, Giovanetti et al.
U.S. Appl. No. 10/582,790, filed Jun. 14, 2006, Giovanetti et al.
U.S. Appl. No. 10/561,018, filed Dec. 16, 2005, Cotarca et al.
U.S. Appl. No. 11/722,056, filed Jun. 18, 2007, Giovanetti et al.
U.S. Appl. No. 10/593,813, filed Sep. 22, 2006, Giovanetti et al.
The Merck Index, Twelfth Edition, No. 4346, p. 733, 1996.
Enders, et al., "Die Pharmakologie einer neuen Gruppe zentral-erregender Substanzen", Arzneimittel Forschung, vol. 10, pp. 243-250, 1960.

* cited by examiner

*Primary Examiner*—Paul A Zucker
(74) *Attorney, Agent, or Firm*—Oblon, Spivak, McClelland, Maier & Neustadt, P.C.

(57) ABSTRACT

The present invention relates to a process for the preparation of gabapentin and, more particularly, it relates to a precipitation process of gabapentin by acidification of an aqueous solution deriving from the Hofmann rearrangement of 1,1-cyclohexanediacetic acid monoamide.

12 Claims, No Drawings

PROCESS FOR THE PREPARATION OF GABAPENTIN

The present invention relates to a process for the preparation of gabapentin and, more particularly, it relates to a precipitation process of gabapentin by acidification of an aqueous solution deriving from the Hofmann rearrangement of 1,1-cyclohexanediacetic acid monoamide.

Gabapentin, 1-(aminomethyl)-cyclohexaneacetic acid (The Merck Index, XII ed., page 733, no. 4343) is a known drug with anti-epileptic activity, described for the first time in U.S. Pat. No. 4,024,175 by Warner-Lambert Co.

In the literature, several processes for the preparation of gabapentin are reported; see for example the already mentioned U.S. Pat. No. 4,024,175, U.S. Pat. No. 5,068,413, and U.S. Pat. No. 5,091,567, both in the name of Gödecke AG.

Substantially all these methods provide for isolation of a gabapentin salt and a final purification step which consists in the treatment of an aqueous solution of said salt (generally hydrochloride) through a weak basic ionic exchange resin, complete evaporation of water from the aqueous gabapentin solution eluted from the resin and crystallization from an alcoholic solvent, generally methanol or methanol/isopropanol or ethanol/ether mixtures.

The U.S. Pat. No. 4,024,175 describes various processes for the preparation of gabapentin or analogous compounds of formula $$H_2N \diagup C \diagdown COOR_1$$
$$(CH_2)_n$$

wherein $R_1$ is a hydrogen atom or a lower alkyl and n is 4, 5 or 6;

characterized by the use of conventional methods for the preparation of primary amines or amino acids such as, for example, the Curtius, Hofmann and Lossen rearrangement.

In particular, the above mentioned patent in the name of Warner Lambert Co., example 4, variant A, column 5, describes the synthesis of the lower cyclic homologous derivative of gabapentin, 1-(methylamino)-1-cyclopentaneacetic acid, through the Hofmann rearrangement of 1,1-cyclopentanediacetic acid monoamide carried out in the presence of sodium hypobromite, acidification and extraction followed by a final purification step of the hydrochloride obtained which consists in the elution through a basic ionic exchange resin and in the recrystallization from alcohol.

The international patent application WO 02/34709 in the name of the same Applicant describes the synthesis of gabapentin by the Hofmann rearrangement of 1,1-cyclohexanediacetic acid monoamide in the presence of sodium hypochlorite, acidification, extraction, purification of the gabapentin hydrochloride obtained through a strong cationic resin and recrystallization.

Moreover, some alternative methods to the use of ionic exchange resin for the conversion of gabapentin hydrochloride into gabapentin have been described.

The patent application WO 98/28255 (Teva) discloses a process for the preparation of gabapentin from the corresponding hydrochloride which comprises the purification of gabapentin hydrochloride from inorganic salts deriving from the synthesis by (a) solubilization of gabapentin hydrochloride in organic solvents in which inorganic salts are insoluble, (b) filtration and (c) optional evaporation of the solvent; the treatment of a gabapentin hydrochloride solution with an amine in a solvent so as to precipitate gabapentin form II, and the crystallization to obtain gabapentin form II.

In the patent application WO 00/58268 (Bioindustria Laboratorio Italiano Medicinali S.p.A.) the separation of the inorganic salts from gabapentin is carried out by diafiltration.

Moreover, the patent application WO 03/070683 (Shasun Chemicals and Drugs Limited) discloses a process for the preparation of gabapentin addition salts with mineral acids such as sulphuric and phosphoric acids and the conversion of said salts into anhydrous gabapentin form II.

Although a variety of methods for the preparation and purification of gabapentin are known, they have some drawbacks.

Processes based on the use of 1,1-cyclohexanediacetic acid derivatives lead prevalently, if not exclusively, to the preparation of a gabapentin salt dissolved in aqueous solution.

Basically for cost-related reasons, in common industrial practice the intermediate gabapentin hydrochloride is generally prepared.

These solutions containing the intermediate salt constitute high volumes of liquids, which are not suitable from the process industrial application point of view.

Moreover, one of the main problems related to the disposal of the scraps produced by these processes is linked to the enormous amount of inorganic anions contained in them.

Said intermediate salt must necessarily be converted into pure gabapentin by purification methods, among which the most widely used at the industrial level is definitely the passage through ionic exchange resins.

In addition to the preparation of pure gabapentin, the treatment is aimed at reducing the content of inorganic salts produced in the isolation step.

The inorganic salts present in the gabapentin hydrochloride aqueous solution are generally sodium salts, such as sodium chloride.

The aforesaid procedure requires a large amount of eluents considering the various steps that usually characterize a chromatographic process, such as feeding the column, eluting the product, washing and regenerating the used resins.

Therefore, it is readily observable that the process, in a way inherent to the common procedure of industrial implementation, takes a long time and high equipment costs and that it produces a considerable quantity of scraps.

It is readily apparent that this procedure entails a particular effort for the disposal system.

Consequently, it becomes necessary to study alternative methods which allow implementing the gabapentin synthesis process in shorter times, limiting the equipments present in the plant and under conditions that allow reducing the quantity of scraps produced.

We have now surprisingly found a process for the preparation of gabapentin at the industrial level which allows, through the direct isolation of gabapentin, to overcome the drawbacks of the processes described by the prior art.

Therefore, object of the present invention is a process for the preparation of gabapentin which comprises:
a. the Hofmann rearrangement of 1,1-cyclohexanediacetic acid monoamide;
b. the precipitation of gabapentin by acidification of the reaction mixture obtained by said rearrangement to a pH comprised between 4 and 6.3 with an organic or inorganic acid.

The process of the present invention comprises a first step wherein the Hofmann rearrangement of 1,1-cyclohexanediacetic acid monoamide is carried out according to known techniques.

Preferably, the Hofmann rearrangement of the monoamide is carried out according to the method described in the aforementioned international patent application WO 02/34709 in the name of the same Applicant.

The reaction mixture obtained at the end of the rearrangement has a pH value around 12 and it is prevalently constituted by gabapentin sodium salt in the form of carbamate (gabapentin present at a concentration which may vary from 10 to 14%), sodium halide and traces of sodium hydroxide.

The acidification reaction of the aqueous mixture obtained is carried out through the use of known organic or inorganic acids, such as acetic, citric, hydrochloric, formic, maleic, methanesulphonic, oxalic and tartaric acid or optionally mixtures thereof.

The acids are generally used in the reaction in pure form, in aqueous solution or in gaseous phase.

The acidification step is preferably carried out with organic acids because their use entails the presence in solution of salts that can be easily eliminated through conventional methods, such as crystallization.

Still more preferably the acidification step is carried out with formic acid, preferably in pure form or in aqueous solution.

Formic acid in aqueous solution is preferably used at a concentration comprised between 85% and 96%.

Use of said acid is particularly favourable from the operative viewpoint because the process carried out in these conditions produces a minimal quantity of residual salt and consequently allows obtaining a highly pure product.

The temperature at which the acidification step is carried out is not a critical parameter.

Preferably, the reaction is carried out at room temperature for an easier and more economical management of the process.

The process of the present invention provides for the post-Hofmann mixture to be acidified at a suitable pH for the aminoacid precipitation in the form of internal salt.

It is known that the gabapentin solubility in water at a temperature of 20° C. is roughly equal to 11% and at 0° C. to about 8.5%.

It is also known that the aminoacid isoelectric point is reached at pH 7.14.

Adding an acid amount necessary to reach the isoelectric point, in the reaction mixture are present: gabapentin, sodium halide (coming directly from the rearrangement) and a mixture of sodium bicarbonate and sodium salt of the utilised acid.

Sodium bicarbonate is the product obtained from the decomposition operated by the utilised acid on the gabapentin carbamate sodium salt, chemical species which is obtained at the end of the rearrangement.

At a pH value corresponding to the aminoacid isoelectric point, the sodium bicarbonate present could decompose to sodium carbonate altering the pH of the aqueous environment, thereby inevitably compromising the efficiency of the process. To avoid this kind of reaction, the mixture obtained by the rearrangement is acidified to such a pH as to allow the complete elimination of the bicarbonate.

Preferably, the reaction mixture is acidified to pH comprised between 5.5 and 6.3.

Still more preferably, the reaction mixture is acidified to pH around 6.2-6.3.

In these conditions, the reaction environment shall prevalently be constituted by: gabapentin, sodium halide, sodium salt of the utilised acid and, probably, traces of the free acid.

It is an advantage from the operative viewpoint the use of a weak and not particular high boiling acid, such as acetic or formic acid, in order to remove any slight excess of said free acid by conventional methods, such as reduced pressure, heating or distillation.

The isolated gabapentin is subjected to crystallization from organic solvents according to conventional techniques.

Preferably, the crystallization step is carried out from alcohols and more preferably from methanol/isopropanol mixtures.

Operatively, one proceeds by identifying the equivalent quantity of acid to be used to bring pH of the post-Hofmann mixture to a value around 6.3.

Then, the predetermined quantity of acid is added to the solution deriving from the Hofmann rearrangement.

Preferably, the solution deriving from the Hofmann rearrangement is added dropwise directly into the predetermined quantity of acid; this operation promotes the precipitation of gabapentin, eliminates the problem of foaming and it makes the reaction easy to reproduce.

The term "added dropwise" also includes the industrial operation of adding small portions.

On the obtained mixture, pH check is performed and pH may be optionally corrected by adding the acid utilised in the process.

The suspension thereby obtained is heated, allowing to eliminate any traces of free acid and to isolate gabapentin by precipitation.

Heating is preferably carried out until the complete dissolution of the suspension is obtained.

The isolated gabapentin is, lastly, crystallized from organic solvents according to conventional techniques.

The process of the present invention allows obtaining gabapentin form II directly from the aqueous solution obtained from the Hofmann rearrangement.

There is no doubt that preparation methods that provide for the isolation of gabapentin in salified form are efficient from the industrial viewpoint, however, they require an additional synthetic step to convert gabapentin salt into free aminoacid.

Therefore, one of the practical advantages deriving from the process described herein is the complete elimination of the purification cycle, which when using ionic exchange resins requires two cycles for each single gabapentin salt charge.

As a consequence of what is described above, all equipments (tanks, columns, evaporators, etc.) connected to purification, and secondarily the work hours dedicated to purification, are eliminated.

Thus, the process of the present invention allows to obtain gabapentin, without appreciable changes in yield, with a lower number of synthetic steps than conventional methods and, consequently, with reduced times and costs.

Moreover, the use of reactants and solvents is considerably reduced, with additional advantages in terms of the disposal of industrial scraps.

The process is very efficient and it allows obtaining a high pure product, almost completely free from the corresponding lactam, a substance endowed with certain toxicity (Von A. Enders et al., Arzneimittel Forschung, 10, (1960), 243-250).

It is therefore readily apparent that the process of the present invention is advantageous with respect to those already described in the literature.

A practical embodiment of the process of the present invention comprises the Hofmann rearrangement of 1,1-cyclohexanediacetic acid monoamide carried out according to conventional methods, the addition of the mixture obtained to a solution of organic acid in such a quantity as to bring the solution pH around a value of 6.3, the control of the reaction mixture pH, the heating of the mixture until the complete dissolution of the resultant suspension, the control of the reaction mixture pH and the precipitation of gabapentin through the gradual cooling thereof. The solid thus precipitated is filtered and washed preferably with an alcoholic solvent, dried and re-crystallized from alcohols according to common techniques.

A preferred practical embodiment of the process of the present invention comprises the Hofmann rearrangement of 1,1-cyclohexanediacetic acid monoamide carried out as described in the international patent application WO 02/34709, mentioned above, in the name of the same Applicant, the addition of the mixture obtained to a solution of organic acid in such a quantity as to bring the solution pH around a value of 6.3, the control of the reaction mixture pH, the heating of the mixture until the complete dissolution of the suspension thus obtained, the control of the reaction mixture pH and the precipitation of gabapentin through the gradual cooling thereof. The solid thus precipitated is filtered and washed preferably with an alcoholic solvent, dried and re-crystallized from alcoholic solvents according to common techniques.

For better illustrating the present invention, the following examples are now given.

EXAMPLE 1

The Hofmann rearrangement of 1,1-cyclohexanediacetic acid monoamide was carried out as described in the international patent application WO 02/34709, example 1, page 3, in the name of the same Applicant.

In a 1 l reactor under nitrogen atmosphere, 80.0 grams of formic acid (1.738 moles, 2.31 eq.) were charged and 1000 grams of the solution obtained from Hofmann rearrangement, containing 12.85% gabapentin (0.750 moles) were added dropwise in 20 minutes at around room temperature.

The pH of the mixture (pH=6.3) was checked and, if necessary, pH was corrected to 6.2-6.3 by adding formic acid.

The solution was heated to 70° C. for the time required to bring everything in solution (about 20-30 minutes).

The temperature of the solution was then brought back to around 50° C. and it was maintained at this level for about 2 hours. The pH of the mixture (pH=6.3) was checked again and, if necessary, pH was corrected to 6.2-6.3 by adding formic acid, maintaining the reaction mixture for further 30 minutes at 50° C.

The temperature of the mixture was brought from 50° C. to 20° C. over a time of about 2 hours and subsequently the temperature was cooled down to about 0° C. in about 1 hour.

The temperature was maintained at 0° C. for about further 2 hours.

The precipitate was filtered, squeezed on the filter and washed with 65 grams of isopropanol cooled to 0° C.

The solid was dried in vacuum oven at 45° C. to give 100.0 grams of crude gabapentin (yield=77%, gabapentin titre=99.5%)

Purification:

In a 1 l reactor under nitrogen atmosphere, 45.0 grams of crude gabapentin, 21.5 grams of demineralised water and 26.6 grams of methanol were charged.

The suspension was heated to 50° C. for 30 minutes, then 111.8 grams of isopropanol were added dropwise into it in 30 minutes.

The suspension remained at 50° C. for further 30 minutes, then it was cooled to 25° C. in about 2 hours and from 25 to 0° C. in about 1 hour.

The temperature was maintained at 0° C. for an additional hour and subsequently the solid was filtered and washed on the filter with 37.0 grams of isopropanol cooled to 0° C.

The product was dried to give 40 grams of crystallized gabapentin (yield=89%, gabapentin titre=100.0%).

Overall yield of the process=67%

EXAMPLE 2

In a 1 l flask under nitrogen atmosphere, 147.2 g of 30% sodium hydroxide solution (equal to 1.106 moles; 1.10 eq.) and 147.2 g of demineralised water were charged.

The solution was cooled up to 0° C. and 200.0 g of 1,1-cyclohexanediacetic acid monoamide (equal to 1.005 moles; 1.00 eq.) were charged in portions.

After charging about two thirds of the monoamide, the additions were continued letting the temperature rise to facilitate dissolution, without ever exceeding 20° C.

Separately, in a 2 l reactor under nitrogen atmosphere, 628.0 g of 12.5% sodium hypochlorite solution (equal to 1.055 moles; 1.05 eq.) containing 1.03% sodium hydroxide (equal to 0.162 moles; 0.16 eq.) and 125.8 g of 30% sodium hydroxide solution (equal to 0.944 moles; 0.94 eq.) were added.

The solution was cooled to −10° C. and 494.0 g of 1,1-cyclohexanediacetic acid monoamide solution in soda were added, maintaining the temperature at −10° C.

At the end, the reaction mixture was maintained at −10° C. for further two hours, then the temperature was brought from −10° C. to 20° C. in four hours, taking care to control any exothermic situations.

The reaction mixture was maintained at 20° C. for further two hours, then the presence of oxidising power was checked with an amido-iodide paper and any excess oxidising power was eliminated adding 0.3 g of sodium metabisulphite.

3 g of activated charcoal were added to the solution, which was kept under stirring for 15 minutes, then filtered under vacuum on a celite bed with a height of about 1 cm.

The resultant solution thus obtained (pH about 12.5) was checked by HPLC titre (useful to predetermine the quantity of acid to be used) and it was ready for the acidification, isolation and crystallization step carried out operating according to what described in Example 1.

EXAMPLE 3

Operating according to what described in Example 1, the precipitation of gabapentin was carried out by replacing formic acid with an equivalent amount of other acids or mixtures thereof.

The results thus obtained were shown in the following Table:

TABLE

| Acid | Yield (%) |
| --- | --- |
| hydrochloric | 63 |
| citric | 62 |
| L-tartaric | 67 |
| maleic | 58 |
| acetic | 57 |
| oxalic | 68 |
| methanesulphonic | 57 |
| formic + hydrochloric (10% molar) | 76 |

The data set out in the table refer to crude gabapentin, i.e. isolated from the precipitation and not crystallized.

The invention claimed is:

1. A process for the preparation of gabapentin which comprises:
   Hofmann rearrangement of 1,1-cyclohexanediacetic acid monoamide to produce a reaction mixture; and
   precipitation of gabapentin from the reaction mixture by acidification of the reaction mixture to a pH of from 4 to 6.3 by the addition of organic acid, inorganic acid, or a mixture thereof.

2. The process according to claim 1, wherein the reaction mixture is acidified to a pH of from 5.5 to 6.3.

3. The process according to claim 1, wherein the reaction mixture is acidified to a pH of from about 6.2 to about 6.3.

4. The process according to claim 1, wherein the acidification of the reaction mixture is carried out by the addition of organic acid.

5. The process according to claim 1, wherein the acidification of the reaction mixture is carried out by the addition of organic acid, wherein the organic acid is one or more organic acids selected from acetic acid, citric acid, formic acid, maleic acid, methanesulphonic acid, oxalic acid and tartaric acid.

6. The process according to claim 1, wherein the acidification of the reaction mixture is carried out by the addition of formic acid.

7. The process according to claim 1, wherein the acidification of the reaction mixture is carried out by the addition of an aqueous solution of formic acid.

8. The process according to claim 7, wherein the aqueous solution of formic acid comprises formic acid in a concentration of from 85% to 96%.

9. The process according to claim 1, wherein the acidification of the reaction mixture is carried out by the addition of inorganic acid.

10. The process according to claim 1, wherein the acidification of the reaction mixture is carried out by the addition of hydrochloric acid.

11. The process according to claim 1, wherein the acidification of the reaction mixture is carried out by the addition of a mixture of organic acid and inorganic acid.

12. The process according to claim 1, wherein the acidification of the reaction mixture is carried out by the addition of a mixture of formic acid and hydrochloric acid.

* * * * *